United States Patent [19]

Auger et al.

[11] Patent Number: 5,610,007
[45] Date of Patent: Mar. 11, 1997

[54] CHIMERIC SHEETS OF EPITHELIAL CELLS

[75] Inventors: François A. Auger; Mahmoud Rouabhia; Louis Lafleur; Lucie Germain, all of Québec, Canada

[73] Assignee: Université Laval, Quebec, Canada

[21] Appl. No.: 7,318

[22] Filed: Jan. 21, 1993

[51] Int. Cl.$^6$ ................... C12N 5/06; A61F 2/10
[52] U.S. Cl. ............ 435/1.1; 424/93.1; 424/93.7; 435/325; 435/346; 435/354; 623/15
[58] Field of Search ............... 435/1, 240.21, 435/240.1, 240.2, 1.1; 623/15; 424/93 R, 93 U, 93.1, 93.7

[56] References Cited

U.S. PATENT DOCUMENTS 4,769,317  6/1988  Hefnon ................... 435/1.1

FOREIGN PATENT DOCUMENTS 2018228  12/1990  Canada .
0364306   4/1990  European Pat. Off. .
2589165   4/1987  France .
9101140   2/1991  WIPO .
9116010  10/1991  WIPO .

OTHER PUBLICATIONS

Y. G. Zhang (1993) Chung Hua Cheng Hsing Shao Shang Wai Ko Tsa Chih (China) 9(1): 37–40, 78. [English Abstract].
R. Cancedda et al. (1993) Year Immunol. 7: 193–198.
J. W. Fabre (1991) Immunology Letters 29:161–166.
Green et al., Growth of Cultured Human epidermal cells into multiple epithelia suitable for grafting; Proc. Natl. Acad. Sci. U.S.A. vol. 76 No. 11, pp. 5665–5668, Nov. 1979.
Gallico et al., Permanent Coverage of Large Burn wounds with autologous cultured human epithelium; The New England Journal of Medicine vol. 311, No. 7, pp. 448–451; Aug. 16, 1984.
David T. Woodley, Covering wounds with cultured keratinocytes; JAMA vol. 262, No. 15, p. 2140–2141, 1989.
Christopher J. Molley et al.; Keratin Polypeptide Expression in Mouse epidermis and cultured epidermal cells; Diffentiation vol. 37, pp. 86–97; 1988.
S. H. Yuspa et al.; Altered differntiation of mouse epidermal cells treated with retinyl acetate in vitro; Experimental Cell Research vol. 86; pp. 95–105, 1974.
ML Tenchini et al.; Culture techniques for human keratinocytes; Burns vol. 18, supplement 1, S11–S15; 1992.
Nicholas E. O'Connor et al., Grafting of Burns with circulated epithelium Prepared from autologous epidermal cells; The Lancet vol. 1, No. 8211, pp. 75–78, Jan. 10, 1981.
David M. Heimbach; Early burn excision and grafting; Surgical clinics of North America vol. 67, No. 1; pp. 93–107; 1987.
James G. Rheinwald, et al.; Serial Cultivation of Strains of Human Epidermal Keratinocytes: the Formation of Keratinizing Colonies from Single Cells; Cell vol. 6, No. 3; pp. 331–343, 1975.

*Primary Examiner*—David Guzo
*Assistant Examiner*—Johnny F. Railey, II
*Attorney, Agent, or Firm*—McAulay Fisher Nissen Goldberg & Kiel, LLP

[57] ABSTRACT

A process for culturing and generating a chimeric cell culture, in particular chimeric epithelium, is disclosed. The chimeric epithelium can be used to treat skin trauma such as burn victims. Autologous epithelial grafts have been used on burn patients although this requires that the patient's cells are cultured and expanded in vitro which generally takes four to five weeks. The chimeric epithelium of the present invention is composed of cells that are both autologous and allogeneic to the host. Therefore, the allogeneic cells can be maintained in a cell bank and co-cultured with autologous host cells when needed. This significantly reduces the time required (by up to 50%) for autologous cell expansion and culture prior to grafting. Furthermore, it has been demonstrated that the allogeneic cells are passively eliminated from the graft without rejection of the total graft.

22 Claims, 2 Drawing Sheets

Fig. 2a     Fig. 2b     Fig. 2c
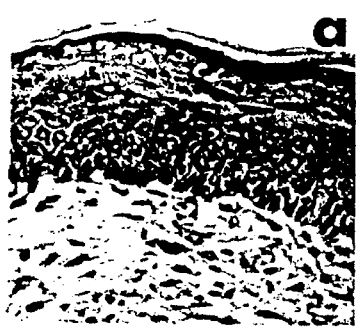  
Fig. 3a     Fig. 3b     Fig. 3c
  

CHIMERIC SHEETS OF EPITHELIAL CELLS

FIELD OF THE INVENTION

The present invention relates to the production of chimeric cell cultures. In particular, the invention relates to the production of chimeric epidermal cell cultures to be used in skin grafting.

BACKGROUND OF THE INVENTION

Uninjured tissues and organs of the body are composed of different cell types, and extracellular matrices that affect cell, tissue and organ functions. Noncongenital injury to cells and tissues causes wounds and initiates common mechanisms of wound healing at all sites in the body (Robbins S. L. et al, (Eds.) "Pathologic Basis of Disease", 2nd ed Philadelphia: W. B. Saunders, 1979:55–106). Fundamental components of wound closure include restoration of stable ectoderm-derived tissue (epithelium or endothelium) and of uniform vascular supply in the adjacent mesoderm-derived tissue. For optimal closure, wounds caused by traumatic injury or elective surgery require rapid restoration of normal tissue anatomy in the absence of infection (Bucknell T. E., et al. (Eds.) "Wound healing for surgeons", Philadelphia: Bailliere Tindall, 1984: 42–74).

In the last decade, technological achievements in the in vitro culture of human epithelial cells has attracted a remarkable interest for its therapeutic application. The most striking practical application is undoubtedly the successful use of in vitro cultured epithelial sheets as autografts on patients with extensive tegumental losses (Green H. et al., 1979, Proc. Natl. Acad. Sci. USA, 76: 5665; Gallico G. et al., 1984, N. Eng. J. Med., 31:448). It has been shown that a biopsy specimen of 1 to 2 cm$^2$ can be expanded in surface area by a factor of 10,000 when cultured in vitro.

Early excision of full skin thickness burns followed by grafting of autologous meshed skin have decreased the mortality rate of patients suffering from large burn wounds (Heimbach D. M., M.D. 1987, Surg. Clin. North. Am., 67: 93). However, burns covering more than 50% of the total body surface lead to very high mortality rates which are directly related to the limited availability of donor sites for epithelium split thickness meshed grafts. In vitro reconstructed human epithelium has been successfully used since 1981 in the treatment of major burns (O'Connor et al, 1981, Lancet, Jan. 10, 1975). This process presents a high level of success for burned patients wounded over 50% of their body surface. However, the long time interval (3 to 5 weeks) required for cell growth and graftable sheets production, a period during which the patient may become progressively ill, is a major disadvantage of this technique. One of our interests is to provide quick and safe methods for skin trauma therapy. This critical goal may be reached by the below described invention.

SUMMARY OF THE INVENTION

The present invention relates to a process for growing and generating chimeric epithelium in vitro for treating skin trauma. A novel aspect of the invention is the use of allogeneic cells in the production of graftable epidermal sheets. These skin grafts can be used to treat a variety of skin trauma, notably burn wounds but also including other conditions such as large congenital nevi, chronic ulceration, nonhealing wounds, and other types of traumatic skin loss that may require therapeutic skin replacement. Indeed for patients who are massively burned the availability of donor skin is the limiting factor for wound coverage and survival. It is predicted that using allogeneic cells would save considerable time (up to 50%) in the production of the chimeric epithelium in vitro since the allogeneic cells can be stored in a skin bank.

Accordingly, the present invention provides a process for producing a chimeric cell culture suitable for transplanting onto a host, said process comprising culturing cells that are autologous to said host with cells that are not autologous to said host under conditions suitable to promote growth of the cells.

The present invention also provides a transplantable chimeric cell culture suitable for transplanting onto a host comprising a mixture of cells that are autologous to said host and cells that are not autologous to said host. In a preferred embodiment, both the cell types are epidermal cells, in particular keratinocytes.

The present invention further provides a use of the chimeric cell culture described above as a skin graft.

The present invention yet also provides a method of transplanting skin comprising grafting onto a patient in need of such treatment the chimeric cell culture described above.

BRIEF DESCRIPTION OF THE DRAWINGS

FIGS. 2a–2c represent the histological analysis of (a) isograft, (b) allogeneic and (c) chimeric grafts on C3H/HeN mice, 14 days post grafting.

FIGS. 3a–3c represent immunofluorescence staining of a chimeric graft and an isograft, 30 days, post grafting, on C3H/HeN. Panel (a) is an isograft stained with H-2$^k$. Panel (b) is a chimeric graft stained with H-2$^k$. Panel (c) is a chimeric graft stained with H-2$^d$.

DETAILED DESCRIPTION OF A PREFERRED EMBODIMENT

Figure 1:
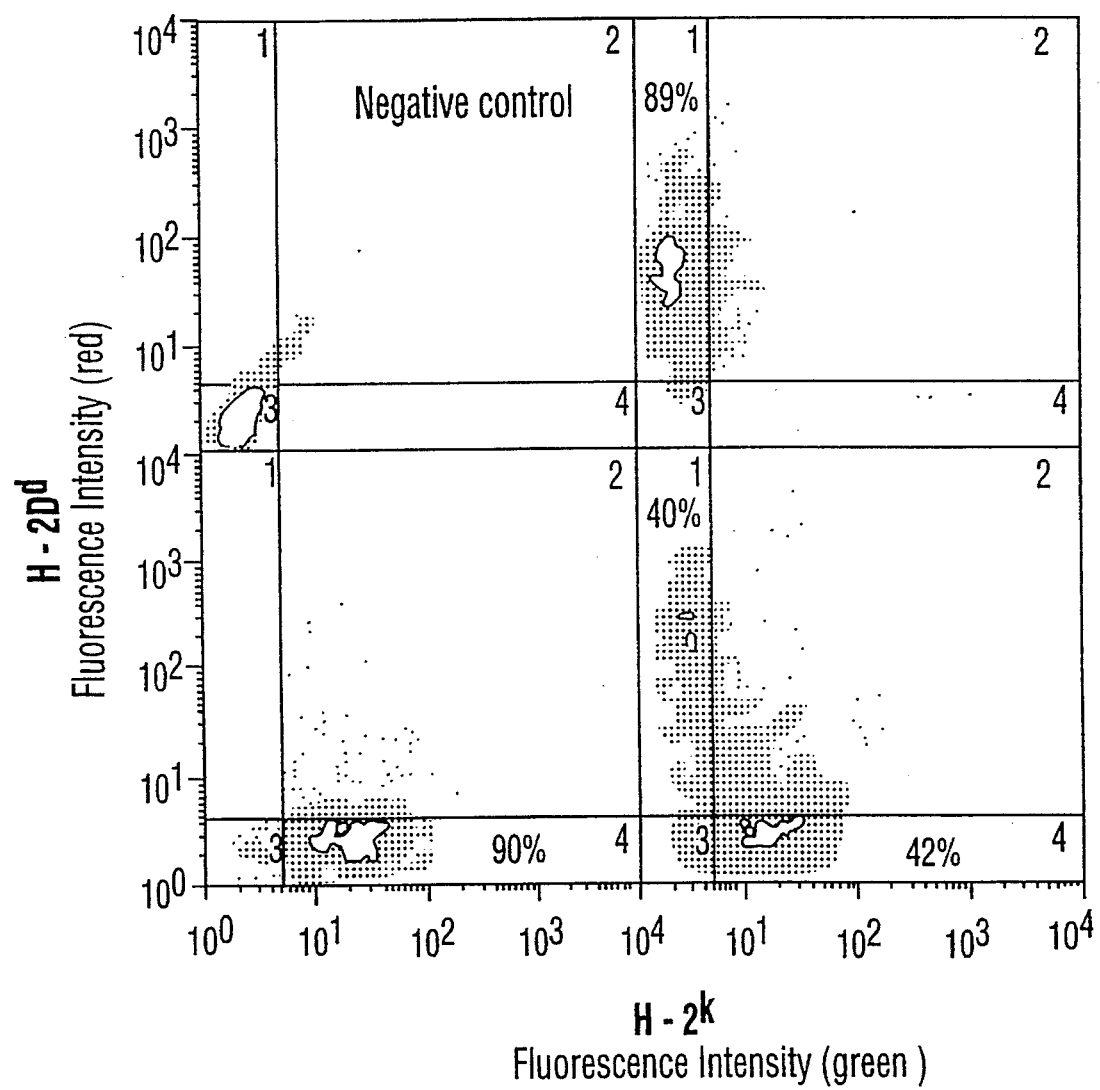
FIG. 1 represents a flow cytometry analysis of various cultures of keratinocytes. Panel (a) represents the percentage of H-2$^d$ positive cells in a pure Balb/c keratinocyte culture. Panel (b) represents the percentage of H-2$^k$ positive cells in a pure C3H/HeN keratinocyte culture. Panel (c) represents the percentage of H-2$^d$ positive and H-2$^k$ positive cells in a chimeric keratinocyte culture.

The following is a description, by way of example, of one embodiment of the present invention wherein murine chimeric epidermal cell cultures are prepared and grafted onto murine hosts.

Epidermal Cell Preparation and Culture

Primary cultures of murine epidermal keratinocytes were established from neonatal Balb/c and C3H/HeN mouse skin according to the method of Yuspa and Harris (Exp. Cell. Res 1974, 86: 95). Briefly, newborn mice were killed by cervical dislocation, then washed 3 times with 70% ethanol, cold proviodine, and 70% ethanol respectively. Limbs and tail were amputated, a longitudinal incision was made from tail to snout, and the skin was removed with forceps. Epidermis was separated from dermis after flotation of the skin on 0.25%–20 μg/ml of trypsin-DNase solution in phosphate buffer saline (PBS) overnight at 4° C. The detached epidermal pieces were aseptically transferred to a medium containing serum to inhibit the action of residual enzyme and to release the epidermal cells mechanically. Single-cell suspensions were washed twice and the pellets were resuspended in 5 ml of 10% FCS medium. The epidermal cell suspensions were applied onto Lympholyte-M gradients (Cedarlane Laboratories Limited, Canada) and spun at room temperature at 300 g for 30 min. The resulting pellet containing keratinous material and other debris was discarded. The interface layer containing nucleated epidermal cells was collected, washed twice, and resuspended in Dulbecco-Vogt modification of Eagle's medium (DME) mixed with Ham's F-12 in 3:1 proportion (Flow Labs, Mississauga, Ontario, Canada). This medium was supplemented with 5 µg/ml of insulin, $10^{-10}$M cholera toxin (Schwarz/Mann, Cleveland, Ohio, U.S.A.), 24.3 µg/ml adenine, 5 µg/ml human transferrin, $2\times10^{-9}$M 3,3',5'-triiodo-L-thyronine (Sigma Chemicals), 0.4 µM of hydrocortisone (Calbiochem, La Jolla, Calif., U.S.A., 100 lU/ml penicillin G, 25 µg/ml gentamicin (Schering Canada Inc.), 10 ng/ml epidermal growth factor (FCS, Flow Lab). Cell viability and a count of the epidermal cell suspension were ascertained by the trypan blue exclusion technique.

Cell Culture

Balb/c keratinocytes (BK) or C3H(CK) were grown individually in culture flasks, or mixed together at 50% BK-50% CK ratio. The seeding cell concentration was $10^5$ cells/cm$^2$. All cultures were allowed to attach for 24 h in a humidified atmosphere with 5% $CO_2$ at 37° C. and then transferred to 31° C., and epidermal growth factor (EGF) was added to the medium. The medium was changed every 2 days. For the first 48 hours of culture, the $Mg^{2+}$ concentration in the medium was adjusted to 2 mM; then it was increased to 5 mM (Molloy C. J. and Laskin J. D., 1988, Differentiation, 37:86).

Immunofluorescence Staining of Chimeric Cultured Cell Suspensions

Confluent cultures were treated with 0.014–0.15% Trypsin-EDTA solution to make cell suspensions. Cells were then treated with an anti-H-$2^k$ monoclonal antibody (specific for C3H/HeN cells) for 45min at 4° C. After two washes with PBS containing 1% bovine serum albumin (BSA) and 0.1% sodium azide (Az), cells were exposed to a goat anti-mouse IgM-IgG-fluorescein (FITC) conjugate (1/300 dilution) for 45 min in the dark at 4° C. Cells were washed and then treated with an anti-H-$2^d$ monoclonal antibody (specific for Balb/c cells) coupled to phycoerytrin (PE) for 45 minutes at 4° C. in the dark. After this incubation, cells were washed 3 times with PBS-1% BSA-0.1% As. Each pellet was then resuspended in 1 ml of 1% paraformaldehyde solution and analyzed by flow cytometry (Becton Dickinson, Montreal, Qc., Canada). As controls, pure Balb/c and C3H/HeN confluent keratinocyte cultures were enzymatically resuspended then stained separately with an anti-H$^d$-PE labelled and H-$2^k$ plus IgM-IgG-F1TC monoclonal antibodies respectively.

Chimeric Sheet Preparation

Epidermal sheets were prepared when the primary cultures of keratinocytes had reached confluence. Cultures were washed twice with sterile PBS; then 5 ml of dispase (Sigma) at 2.5 mg/ml were added to each flask and incubated at 37° C. for 20 to 30 minutes, to release these sheets from the flask's surface. Sheets were washed twice and transferred to a vaseline gauze (Ethicon Ltd, Johnson and Johnson, Peterborough Ont., Canada) basal side up and then fixed with Ligaclips (Sherwood Medical Industries Ltd, Markham, Ont., Canada). These sheets were left immersed in the appropriate medium until grafting.

Transplantation Procedures

The recipient mice used in the transplantation experiments were Balb/c and C3H/HeN mice. Each strain received transplants of epidermal sheets that were (a) isologous, (b) allogeneic or (c) chimeric to the mouse receiving the transplant. For example, Balb/c mice were transplanted with epidermal sheets derived from (a) Balb/c mice (isologous transplant or isograft), (b) C3H/HeN mice (allogeneic graft) or (c) both Balb/c and C3H/HeN mice (chimeric graft).

Inbred strains of mice, such as Balb/c and C3H/HeN mice, represent a homogeneous population wherein all members of one strain have the identical genetic make up. Therefore, it can be appreciated that an isograft can be considered as an experimental equivalent to an autograft since, in both situations, both the recipient and the transplant are of the same genetic make up. For the purposes of the present experiments, isografts were used instead of autografts, since the mice from which the epidermal sheets are prepared are sacrificed when the epidermal cells are isolated.

Recipient mice were anaesthetized with an intramuscular injection of ketamine xylazine at 0.05 ml/10 g weight. Mouse dorsum was prepared for grafting by shaving and washing the area with proviodine and 70% ethanol. Full thickness skin was excised down to the muscle. A Fusenig transplantation chamber (Fusenig N. E. et al. 1980. In: "Tissue Culture in Medical Research", Vol. 2, Richard R. G. and Rayan K. (Eds), Oxford, Pergamon. pp 87) was installed and a homogenous or chimeric sheet was deposited over the muscle. The vaseline gauze was then gently detached. The top of the transplantation chamber was installed and fixed by four cutaneous stitches (silk 4-0 from Ethicon Ltd., Peterborough, Ont.) for five days and then removed. Fourteen and thirty days after grafting, biopsies were taken for histology and immunohistochemical analysis.

Histological Studies

Fourteen days post grafting, biopsies were harvested from the isograft and the allogeneic and chimeric grafts, fixed in Bouin's solution and embedded in paraffin. Then 4–5 µm sections were stained with hematoxylin phloxine and saffron, and observed under an optic microscope (Nikon Optiphot, Japan).

For indirect immunofluorescence, intact biopsies were harvested 30 days postgrafting from the isograft and the chimeric implants, embedded in OCT compound (Miles, Elkhart, Ind.), frozen in liquid nitrogen, and stored at −70° C. until needed. Four µm cryostat sections were prepared from each biopsy and stained with anti-H-$2^d$ or anti-H-$2^k$ monoclonal antibodies for 45 minutes at room temperature in a 95% humidified chamber, rinsed extensively with PBS-BSA-As, and then overlaid with F1TC-conjugated goat anti-mouse IgM-IgG for 45 minutes as above in the dark. Following further rinsing with PBS-BSA-Az, sections were mounted in 30% glycerol-2% glycine-PBS solution, overlaid with a coverslip, examined using a fluorescence microscope (Nikon Optiphot), and photographed with Kodak Tmax 400 ASA film.

Results

The inventors have developed a new epithelial culture method to produce chimeric graftable sheets composed of two different keratinocyte types, using a murine model.

These graftable sheets should have use in treating and accelerating burn therapy as well as treating other dermatological trauma.

The chimeric cultures, comprising a 50:50 mixture of Balb/c and C3H/HeN keratinocytes were co-cultured until confluence. The confluent cultures were either (i) stained to assess the percentage of each cell type on these graftable chimeric sheets, using specific anti-H-$2^d$ (for Balb/c) and/or anti-H-$2^k$ (for C3H/HeN) monoclonal antibodies, or (ii) epithelia were obtained from confluent cultures by dispase treatment and grafted onto recipient Balb/c or C3H/HeN male mice 6 to 8 weeks old. FIG. 1 shows that the chimeric culture contains approximately the same proportions of each cell type after 3 days of culture when assessed with both anti-H-$2^d$ and anti-H-$2^k$ monoclonal antibodies used in combination, or with each antibody used individually. As shown in panel (c), the percentage of Balb/c keratinocytes in the chimeric culture was 40% while the percentage of C3H/HeN keratinocytes was 42%. This immunostaining shows no growth inhibition of the Balb/c keratinocyte (BK) proliferation when co-cultured with the C3H/HeN keratinocytes (CK) and vice versa. Furthermore, the epithelial sheets ready for grafting were composed of the two cell types essentially at the same ratio as at the beginning of the culture seeding. The negative control represents staining with the second antibody, Anti-Mouse-IgG-FITC, only.

Chimeric sheets were grafted and left on the recipient dorsus. Fourteen days postgrafting, biopsies were taken from the isograft and the allogeneic and chimeric grafts for histological analysis. The hematoxylin and phloxine staining (FIG. 2) showed a well structured epidermis with the presence of stratum corneum, stratum spinosum and stratum germinativum. No monocyte infiltration was observed in the chimeric graft or the isograft. However, the cultured epithelium allografts showed disorganized epithelial cells and an important monocyte and polymorphonuclear cell infiltration which is a sign of the implant rejection. The chimeric graft and the isograft were not rejected.

In order to determine the origin of the keratinocytes which constitute the epidermis after a chimeric sheet grafting, biopsies from the autologous and the chimeric implant were taken at the 30th day post grafting, embedded on OCT and frozen in liquid nitrogen. Thin sections were prepared from each biopsy and stained with an anti-H-$2^d$ or anti-H-$2^k$ monoclonal antibody. As shown in FIG. 3, chimeric sheets previously grafted on Balb/c recipient mice showed that the epidermis contains only Balb/c (BK) cells as in the isograft. No C3H/HeN (CK) cells remained in the transplant. The CK cells were passively eliminated from the transplant without the usual rejection of the whole implant. The same results were obtained after the transplantation of chimeric sheets on C3H/HeN recipient mice.

The inventors have also shown that similar results have been obtained when the chimeric culture consists of as little as 25% of isologous cells, with 75% allogeneic cells. Therefore, this invention for generating chimeric epidermis using isologous and allogeneic epidermal cell suspensions shows high quality results for skin replacement.

It is predicted that using this technology for human treatment could significantly cut down the delay in time required to obtain graftable sheets by approximately 50%. Indeed, in the presence of the feeder layer of 3T3 fibroblasts, freshly isolated keratinocytes grow in colonies through many cycles of cell division (Rheinwald J. G. and Green H., 1975, Cell, 6: 331). The size of colonies increases with time until they fuse and give rise to continuous multilayered sheets of keratinocytes in approximately 10 days. At this time, proliferation stops (Tenchini et al. 1992, Burns, 18: 11a). In parallel, allogeneic keratinocytes stored in a cell bank, beforehand tested for virus infection and other diseases, may be thawed and plated onto culture flasks until confluence. Cell suspensions can be made separately from both the autologous and allogeneic cultures. The two cell types can then be mixed together at an appropriate ratio and then plated in new flasks and incubated for graftable sheet production. At this stage, the epithelial sheets produced will be used for skin trauma therapy such as in burns. Compared to the standard culture methods, the chimeric sheets could be used for grafting on the first passage of cultured autologous keratinocytes rather than waiting for the second or, in many cases, the third passage. This method should allow significant reduction in the skin wound treatment duration.

While the above description relates to chimeric skin grafts it is predicted that this chimeric technology could also be used for preparing chimeric vascular organs, chimeric ligaments as well as other chimeric organs.

What we claim as our invention is:

1. A process for producing a chimeric sheet of epithelial cells suitable for transplanting onto a host, said process comprising the steps of:

mixing together in vitro epithelial cells that are autologous to said host with epithelial cells that are either allogeneic or xenogeneic to said host, and culturing the mixture of epithelial cells in vitro under conditions suitable to promote confluent growth in the epithelial cells into a chimeric sheet of epithelial cells suitable for transplanting onto a host.

2. The process according to claim 1 wherein said epithelial cells are epidermal cells.

3. The process according to claim 2 wherein said epidermal cells are keratinocytes.

4. The process according to claim 3 wherein the chimeric sheet of epithelial cells is suitable for skin grafts.

5. A chimeric sheet of epithelial cells produced in vitro by the process of claim 1 comprising a mixture of epithelial cells that are autologous to said host and epithelial cells that are allogeneic or xenogeneic to said host.

6. A chimeric sheet of epithelial cells produced in vitro by the process of claim 2 comprising a mixture of epithelial cells that are autologous to said host and epithelial cells that are allogeneic or xenogeneic to said host.

7. A chimeric sheet of epithelial cells produced in vitro by the process of claim 3 comprising a mixture of epithelial cells that are autologous to said host and epithelial cells that are allogeneic or xenogeneic to said host.

8. A chimeric sheet of epithelial cells produced in vitro by the process of claim 4 comprising a mixture of epithelial cells that are autologous to said host and epithelial cells that are allogeneic or xenogeneic to said host.

9. A chimeric sheet of epithelial cells suitable for transplanting onto a host comprising a cultured mixture of epithelial cells that are autologous to said host and epithelial cells that are allogeneic or xenogeneic to said host.

10. The chimeric sheet of epithelial cells according to claim 5 wherein said epithelial cells that are not autologous to said host are allogeneic to said host.

11. The chimeric sheet of epithelial cells according to claim 5 wherein said epithelial cells are epidermal cells.

12. The chimeric sheet of epithelial cells according to claim 11 wherein said epidermal cells are keratinocytes.

13. The chimeric sheet of epithelial cells according to claim 12 wherein said chimeric sheet of epithelial cells is suitable for skin grafts.

14. A process for producing a chimeric sheet of epithelial cells suitable for transplanting onto a host, said process consisting of the steps of:

mixing together in vitro epithelial cells that are autologous to said host with epithelial cells that are allogeneic to said host, wherein said autologous epithelial cells are 50% of the epithelial cells in the culture and said allogeneic cells are 50% of the epithelial cells in the culture, and culturing the epithelial cells in vitro under conditions suitable to promote confluent growth of the epithelial cells into a chimeric sheet of epithelial cells suitable for transplanting onto the autologous host.

15. The process according to claim 14 wherein said epithelial cells are epidermal cells.

16. The process according to claim 15 wherein said epidermal cells are keratinocytes.

17. The process according to claim 16 wherein the chimeric sheet of epithelial cells is suitable for skin grafts.

18. A process for producing a chimeric sheet of epithelial cells suitable for transplanting onto a host, said process consisting of the steps of:

mixing together in vitro epithelial cells that are autologous to said host with epithelial cells that are allogeneic to said host, wherein said autologous epithelial cells are 25% of the epithelial cells in the culture and said allogeneic epithelial cells are 75% of the epithelial cells in the culture, and culturing the epithelial cells in vitro under conditions suitable to promote confluent growth of the epithelial cells in a chimeric sheet of epithelial cells suitable for transplanting onto the autologous host.

19. The process according to claim 18 wherein said epithelial cells are epidermal cells.

20. The process according to claim 19 wherein said epidermal cells are keratinocytes.

21. The process according to claim 20 wherein the chimeric sheet of epithelial cells is suitable for skin grafts.

22. A chimeric sheet of epithelial cells produced in vitro by the process of claim 14.

* * * * *